(12) United States Patent  (10) Patent No.: US 9,098,993 B2
Reed, Jr.  (45) Date of Patent: Aug. 4, 2015

(54) PATIENT MONITORING SYSTEM FOR BATHROOM

(71) Applicant: DRS Medical Devices, LLC, Fort Wayne, IN (US)

(72) Inventor: Donald N. Reed, Jr., Fort Wayne, IN (US)

(73) Assignee: DRS Medical Devices, LLC, Fort Wayne, IN (US)

( * ) Notice: Subject to any disclaimer, the term of this patent is extended or adjusted under 35 U.S.C. 154(b) by 0 days.

(21) Appl. No.: 14/447,390

(22) Filed: Jul. 30, 2014

(65) Prior Publication Data

US 2014/0340227 A1 Nov. 20, 2014

Related U.S. Application Data

(63) Continuation-in-part of application No. 13/565,428, filed on Aug. 2, 2012, now Pat. No. 8,823,529.

(51) Int. Cl.
*G08B 23/00* (2006.01)
*G08B 21/22* (2006.01)
*A61B 5/11* (2006.01)
(Continued)

(52) U.S. Cl.
CPC .............. *G08B 21/22* (2013.01); *A61B 5/1115* (2013.01); *A61B 5/6889* (2013.01); *G08B 21/0469* (2013.01)

(58) Field of Classification Search
CPC ............................ G08B 21/22; G08B 21/0469
USPC ............... 340/521, 539.11, 539.23, 506, 541, 340/542, 548, 568; 702/150, 151
See application file for complete search history.

(56) References Cited

U.S. PATENT DOCUMENTS 4,196,425 A 4/1980 Williams, Jr. et al.
4,638,307 A 1/1987 Swartout
(Continued)

FOREIGN PATENT DOCUMENTS

WO WO 01/95280 A1 12/2001
WO WO 2009/029996 A1 3/2009

OTHER PUBLICATIONS

Jasco Products Company, LLC, 45129 GE Wireless Alarm System Control Center User's Manual Choice Alert, 20 pages, Nov. 2, 2007.

(Continued)

*Primary Examiner* — Tai T Nguyen
(74) *Attorney, Agent, or Firm* — Bose McKinney & Evans LLP

(57) ABSTRACT

A patient monitoring system adapted for use with a bathroom. The system includes a motion detection unit including a motion detection sensor and a first housing. The system also includes an alarm unit having an alarm device and a second housing. Control circuitry operably couples the motion detection sensor with the alarm device. The control circuitry is configured to activate the alarm device when the motion detection sensor detects motion. The system also includes a support structure removably mounted on the bathroom door wherein the support structure is adapted to support the first housing proximate the interior surface of the door and support the second housing proximate the exterior surface of the door. The motion detection sensor is positioned so that when a fall-risk patient begins to rise from the toilet, the alarm device will alert a caregiver outside the bathroom who may then assist the patient.

20 Claims, 10 Drawing Sheets

(51) Int. Cl.
*G08B 21/04* (2006.01)
*A61B 5/00* (2006.01)

(56) References Cited

U.S. PATENT DOCUMENTS

| | | | |
|---|---|---|---|
| 4,716,402 A | 12/1987 | Francis | |
| 4,843,374 A | 6/1989 | Sansky | |
| 4,947,152 A | 8/1990 | Hodges | |
| 4,951,032 A | 8/1990 | Langsam | |
| 5,371,489 A | 12/1994 | Carroll et al. | |
| 5,434,556 A | 7/1995 | Donohoo | |
| 5,471,198 A | 11/1995 | Newham | |
| 5,600,305 A | 2/1997 | Stafford et al. | |
| 5,633,627 A | 5/1997 | Newham | |
| 5,640,145 A | 6/1997 | Newham | |
| 5,654,694 A | 8/1997 | Newham | |
| 5,751,214 A * | 5/1998 | Cowley et al. | 340/573.4 |
| 6,111,509 A | 8/2000 | Holmes | |
| 6,204,767 B1 | 3/2001 | Sparks | |
| 6,441,742 B1 | 8/2002 | Lovely et al. | |
| 6,741,163 B1 | 5/2004 | Roberts | |
| 6,788,206 B1 | 9/2004 | Edwards | |
| 6,812,836 B2 | 11/2004 | Soloway et al. | |
| 6,950,017 B2 | 9/2005 | Smith | |
| 7,012,533 B2 | 3/2006 | Younse | |
| 7,132,941 B2 | 11/2006 | Sherlock | |
| 7,151,457 B2 | 12/2006 | Riley et al. | |
| 7,268,682 B2 | 9/2007 | Bialecki, Jr. et al. | |
| 7,443,304 B2 | 10/2008 | Rowe et al. | |
| 7,733,228 B2 | 6/2010 | Lee et al. | |
| 7,764,167 B2 | 7/2010 | Reeves et al. | |
| 7,916,018 B2 | 3/2011 | Eskildsen et al. | |
| 7,920,061 B2 | 4/2011 | Klein et al. | |
| 7,987,069 B2 | 7/2011 | Rodgers et al. | |
| 8,655,547 B1 | 2/2014 | Steele | |
| 2007/0040692 A1 | 2/2007 | Smith et al. | |
| 2008/0204258 A1 | 8/2008 | Dayton et al. | |
| 2010/0033331 A1 | 2/2010 | Bautovich | |

OTHER PUBLICATIONS

Jasco Products Company, LLC, 45132 GE Wireless Alarm System Motion Sensor User's Manual Choice Alert, 16 pages, Jan. 18, 2008.
Jasco Products Company, LLC, 45137 GE Wireless Alarm System Silent Alert User's Manual Choice Alert, 12 pages, Jan. 9, 2008.
Posey Company, Posey KeepSafe Alarm, 2 pages, Arcadia, CA 2012.
Posey Company, Posey KeepSafe Essential Door Guard Alarm/Do Not Enter Banner Alarm, 2 pages, Arcadia, CA 2012.
Posey Company, Sitter Elite Instruction Manual, 40 pages, Arcadia, CA, 2011.
Posey Company, Posey Door Guard/Do Not Enter Alarm, 2 pages, Arcadia, CA 2010.

* cited by examiner

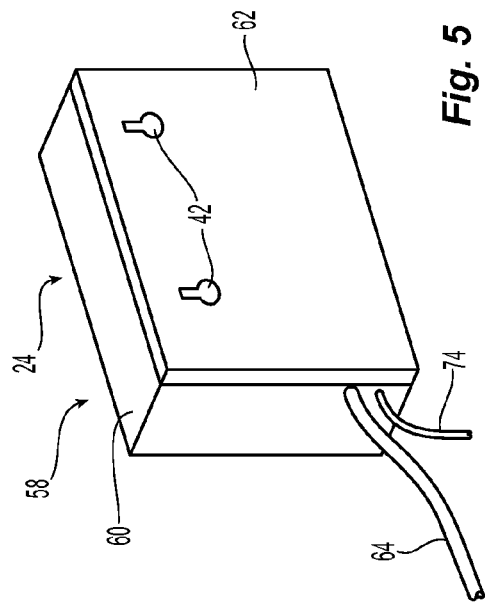
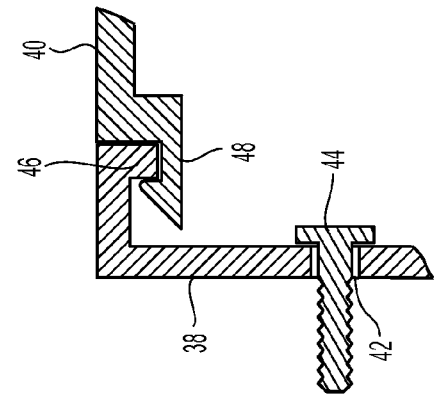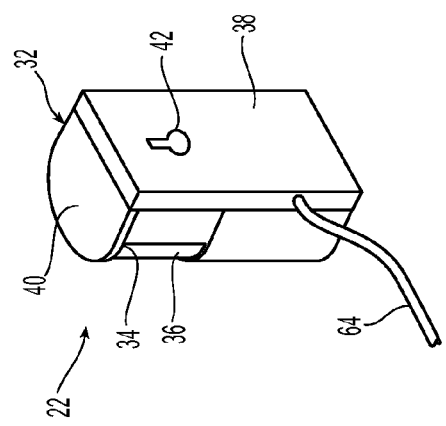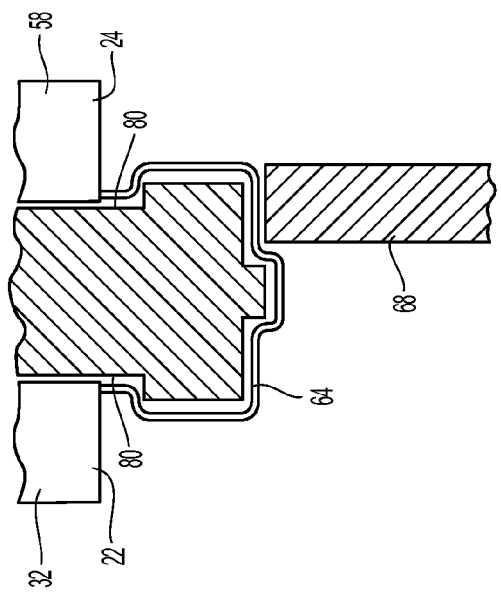
Fig. 5
Fig. 7
Fig. 6
Fig. 4

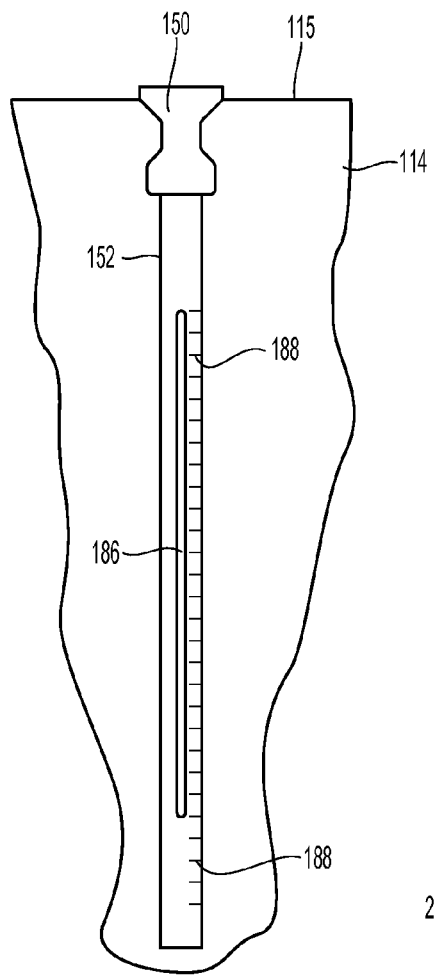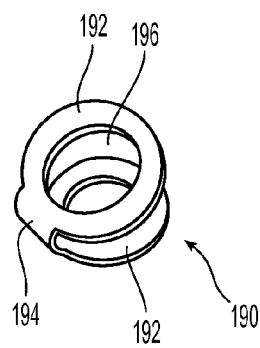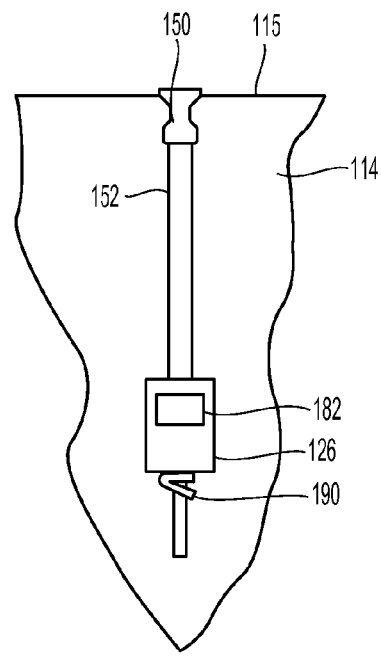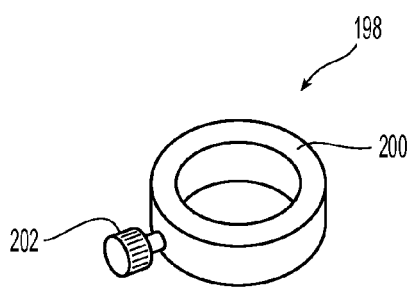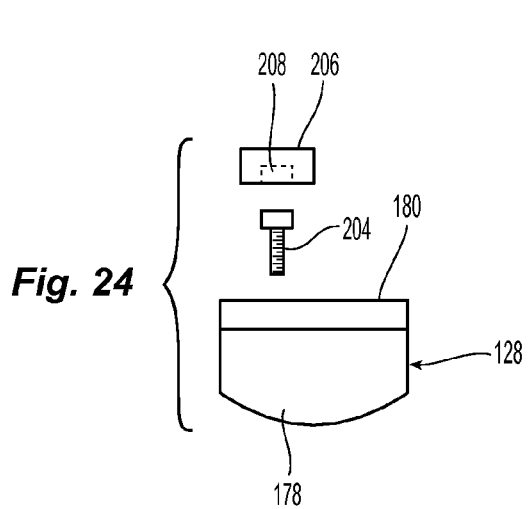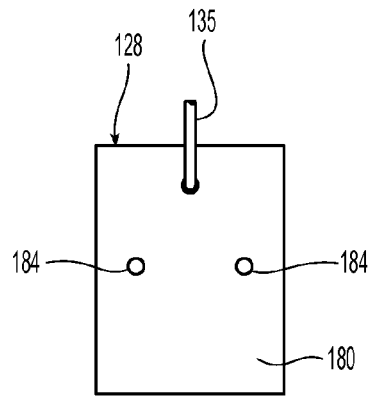
*Fig. 19*
*Fig. 21*
*Fig. 20*
*Fig. 22*
*Fig. 24*
*Fig. 23*

PATIENT MONITORING SYSTEM FOR BATHROOM

CROSS REFERENCE TO RELATED APPLICATIONS

This is a continuation-in-part of application Ser. No. 13/565,428 filed Aug. 2, 2012 which is now U.S. Pat. No. 8,823,529 entitled PATIENT MOVEMENT MONITORING SYSTEM the disclosure of which is incorporated herein by reference.

BACKGROUND OF THE INVENTION

1. Field of the Invention

The present invention relates to systems which monitor patient movement and, more particularly, to systems which can be used to alert a caregiver when a patient using a bathroom attempts to stand without assistance.

2. Description of the Related Art

Care facilities, such as hospitals, long-term care facilities, and elderly care facilities, have many patients that present a "fall-risk." For example, some elderly patients are still ambulatory but are unstable on their feet. If such patients fall from a standing position or while getting out of bed they can break bones, e.g., a hip or rib, or otherwise significantly injure themselves. Such patients do not always follow the instructions of caregivers and may attempt to get out of their bed or walk unassisted despite contrary health-care instructions.

A variety of monitoring systems are known for such "fall-risk" patients. For example, pads which are capable of detecting weight may be placed on the bed and generate an alarm signal when a weight is removed from the pad, e.g., when a patient moves off of the pad. Such pads, however, have not always proven to be effective for lighter weight patients. Some such pads have also been known to have only a short useful life before becoming worn and unreliable.

It is also known to use motion detectors to determine when a fall-risk patient has exited a bed. Many of the systems employing motion detectors can be relatively expensive and many care facilities find the deployment of such systems to be cost-prohibitive.

While a variety of patient monitors are known in the art, further improvements in such monitoring systems are desirable.

SUMMARY OF THE INVENTION

The present invention provides a patient monitoring system that can help prevent falls from taking place in a bathroom.

One situation that represents a significant proportion of all patient falls occurs when a fall-risk patient uses the bathroom. Typically, a nurse or other care giver will escort the patient to the bathroom. Oftentimes, the caregiver will assist the patient in taking a seated position on the toilet and will then step out of the bathroom and close the door to provide the patient with privacy. The caregiver will typically stand immediately outside the closed door and instruct the patient to notify the caregiver when they are ready to be assisted in rising from the toilet. Many patients, however, will ignore the caregiver's instructions and attempt to rise from the toilet without notifying the caregiver. Many falls occur when such patients attempt to rise from the toilet without caregiver assistance.

The present invention provides a system that can alert the caregiver when the patient attempts to arise from the toilet without assistance and thereby allow the caregiver to enter the bathroom and provide the patient with assistance as the patient arises from the toilet.

The invention comprises, in one form thereof, a patient monitoring system adapted for use with a bathroom having a toilet wherein a doorway provides entry into the bathroom and a door is moveably mounted in the doorway and wherein, when the door is in a closed position, the door has an interior surface facing into the bathroom and an opposing exterior surface facing away from the bathroom. The system includes a motion detection unit including a motion detection sensor and a first housing supporting the motion detection sensor, an alarm unit having an alarm device and a second housing supporting the alarm device and control circuitry operably coupling the motion detection sensor with the alarm device, the control circuitry being configured to activate the alarm device when the motion detection sensor detects motion. The system also includes a support structure removably supportable on the door wherein the support structure is adapted to support the first housing proximate the interior surface of the door and support the second housing proximate the exterior surface of the door.

The invention comprises, in another form thereof, a patient monitoring system adapted for use with a bathroom having a toilet wherein a doorway provides entry into the bathroom and a door is moveably mounted in the doorway and wherein, when the door is in a closed position, the door has an interior surface facing into the bathroom and an opposing exterior surface facing away from the bathroom. The system includes a motion detection unit including a motion detection sensor and a first housing supporting the motion detection sensor, an alarm unit having an alarm device and a second housing supporting the alarm device, and control circuitry operably coupling the motion detection sensor with the alarm device, the control circuitry being configured to activate the alarm device when the motion detection sensor detects motion. A manually operated switch is supported on the second housing with the switch being operably coupled with the motion detection sensor and the control circuitry wherein the switch selectively activates and deactivates the system. The system also includes a support structure removably supportable on the door. The support structure includes an engagement portion adapted to extend over and engage the top edge of the door and thereby mount the support structure on the door and first and second elongate members extending from opposite sides of the engagement portion whereby the first elongate member is positionable proximate the interior surface of the door and the second elongate member is positionable proximate the exterior surface of the door when the support structure is mounted on the door. The first housing is supportable on the first elongate member proximate the interior surface of the door and the second housing is supportable on the second elongate member proximate the exterior surface of the door. The first elongate member defines a first axis and the first housing is axially repositionable on the first elongate member. The first housing is also angularly repositionable on the first elongate member about a yaw axis substantially parallel to the first axis. The motion detection sensor defines a detection zone wherein the motion detection sensor is positionable to extend the detection zone over the toilet whereby a patient seated on the toilet will be located below the detection zone without intruding into the detection zone. When the patient rises from the toilet, the patient will enter the detection zone thereby activating the alarm device whereby a caregiver positioned outside the bathroom proximate the door with the door in the closed position will be notified by the alarm device.

In some embodiments, the control circuitry is disposed in the second housing and each of the first and second housings have a removeable power source wherein the removable power source in the first housing powers the motion control sensor and the power source in the second housing powers the control circuitry and the alarm device. The alarm device in such an embodiment may take the form of an LED light and wiring may extend between the first and second housings with the first and second elongate members each defining a hollow interior for routing the wiring at least part of the distance between the first and second housings.

In still other embodiments, the system may include a plurality of shim members selectively attachable to the first housing and positionable between the first housing the interior surface of the door to thereby define an angular position of first housing about the yaw axis. Each of the plurality of shim members has a different configuration whereby each of the plurality of shim members defines a different angular position for the first housing about the yaw axis.

The invention comprises, in yet another embodiment thereof, a method of monitoring a patient in a bathroom having a toilet and wherein a door is moveably mounted in a doorway, the doorway providing access to the bathroom when the door is in an open position and the door blocks access through the doorway when the door is in a closed position, and wherein, when the door is in the closed position, the door has an interior surface facing the bathroom and an exterior surface facing away from the bathroom. The method includes mounting a support structure on the door and attaching a first housing to the support structure proximate the interior surface of the door wherein the first housing supports a motion detector sensor. The method also includes positioning the motion detector sensor wherein the motion detection sensor defines a detection zone extending over the toilet and having a lower boundary spaced above the toilet wherein a patient seated on the toilet will be located below the detection zone without intruding into the detection zone and when the patient rises from the toilet the patient will enter the detection zone. A second housing is attached to the support structure proximate the exterior surface of the door wherein the second housing supports an alarm device. And the method further includes providing control circuitry to operably couple the motion detection sensor with the alarm device, the control circuitry being configured to activate the alarm device when the motion detection sensor detects motion whereby a caregiver positioned outside the bathroom proximate the door with the door in the closed position will be notified by the alarm device when the patient rises from the toilet.

In some embodiments of the method, the step of positioning the motion detector sensor includes selectively adjusting the vertical position of the motion detection sensor on the support structure. In still other embodiments of the method, the step of positioning the motion detector sensor includes selectively adjusting the angular position of the motion detection sensor about a vertically extending yaw axis.

In some embodiments, the method further includes the step of selectively activating and de-activating the system with a switch supported on the second housing.

In yet other embodiments of the method, the step of mounting a support structure on the door includes engaging a portion of the support structure with a top edge of the door to mount the support structure on the door. In some varients of this embodiment, the method may further include the step of extending wiring between the first and second housings to operably couple the motion detection sensor with the alarm device wherein the wiring is extended over the top edge of the door.

BRIEF DESCRIPTION OF THE DRAWINGS

The above mentioned and other features of this invention, and the manner of attaining them, will become more apparent and the invention itself will be better understood by reference to the following description of an embodiment of the invention taken in conjunction with the accompanying drawings, wherein:

FIG. 4 is a rear perspective view of a motion detection unit.

FIG. 5 is a rear perspective view of a control unit.

FIG. 6 is a schematic cross sectional view through a door jamb.

FIG. 7 is a partial view of a housing.

FIG. 19 is a frontal view of the support structure on a door from inside the bathroom.

FIG. 20 is a frontal view of the support structure with a motion detection unit mounted thereon from inside the bathroom.

FIG. 21 is a repositionable stop member that can be used to adjust the height of the motion detection unit and/or the alarm unit.

FIG. 22 is an alternative embodiment of a repositionable stop member.

FIG. 23 is a back view of the motion detection unit.

FIG. 24 is an exploded top view of a motion detection unit with an adjustable foot for controlling the angular position of the motion detection unit.

Figure 1:
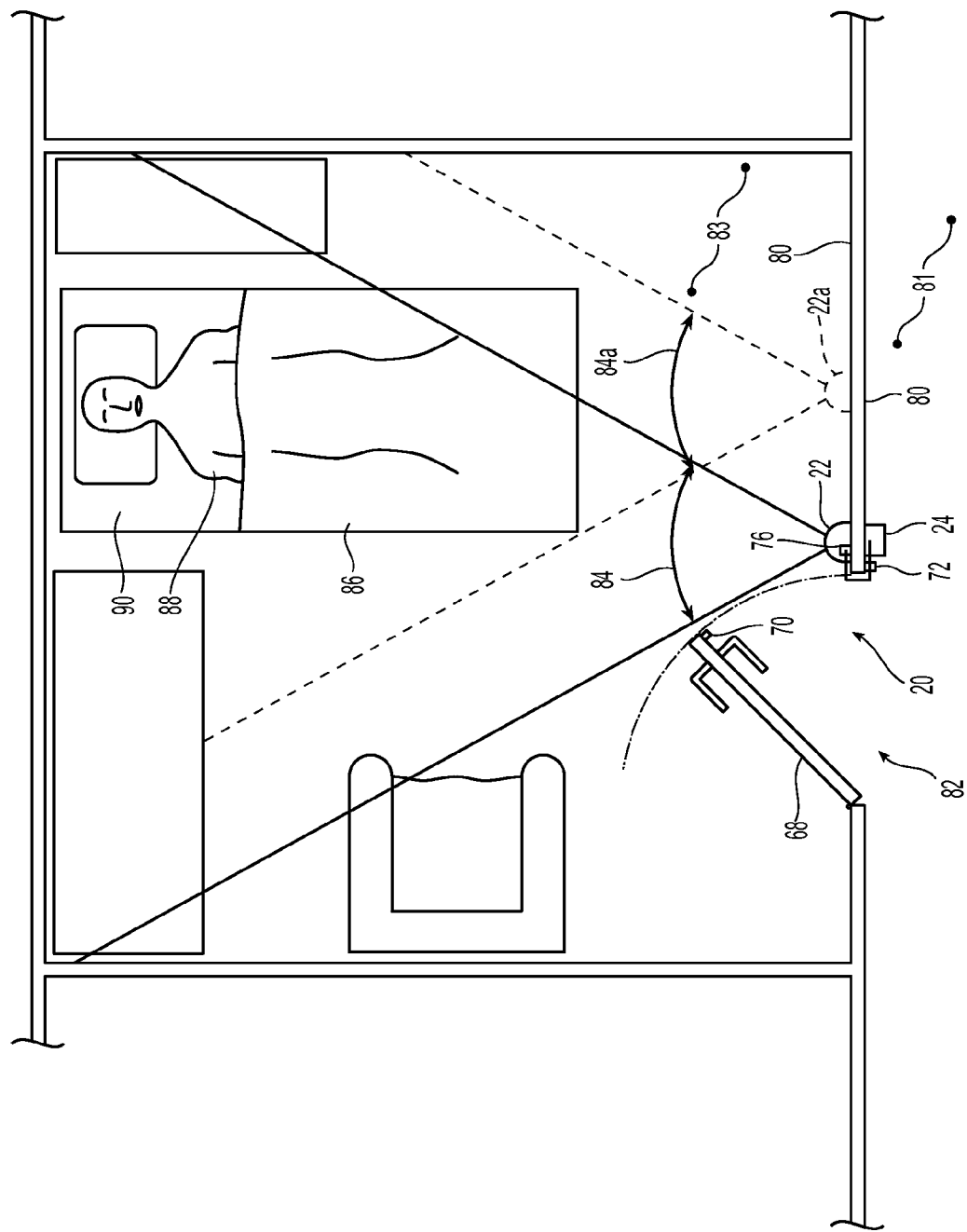
FIG. 1 is a schematic plan view of a hospital room with an installed patient monitoring system.
Figure 2:
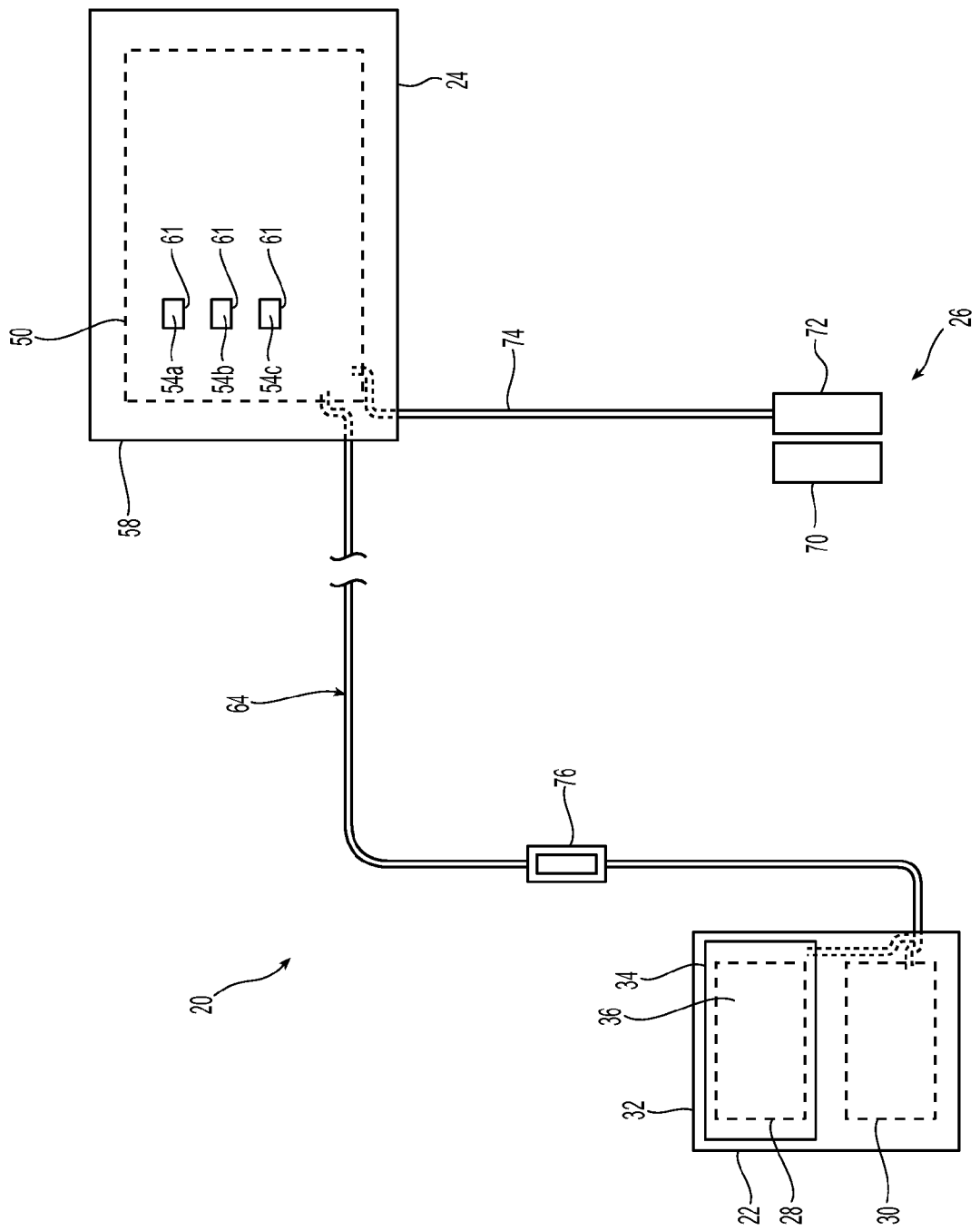
FIG. 2 is a schematic view of a patient monitoring system.
Figure 3:
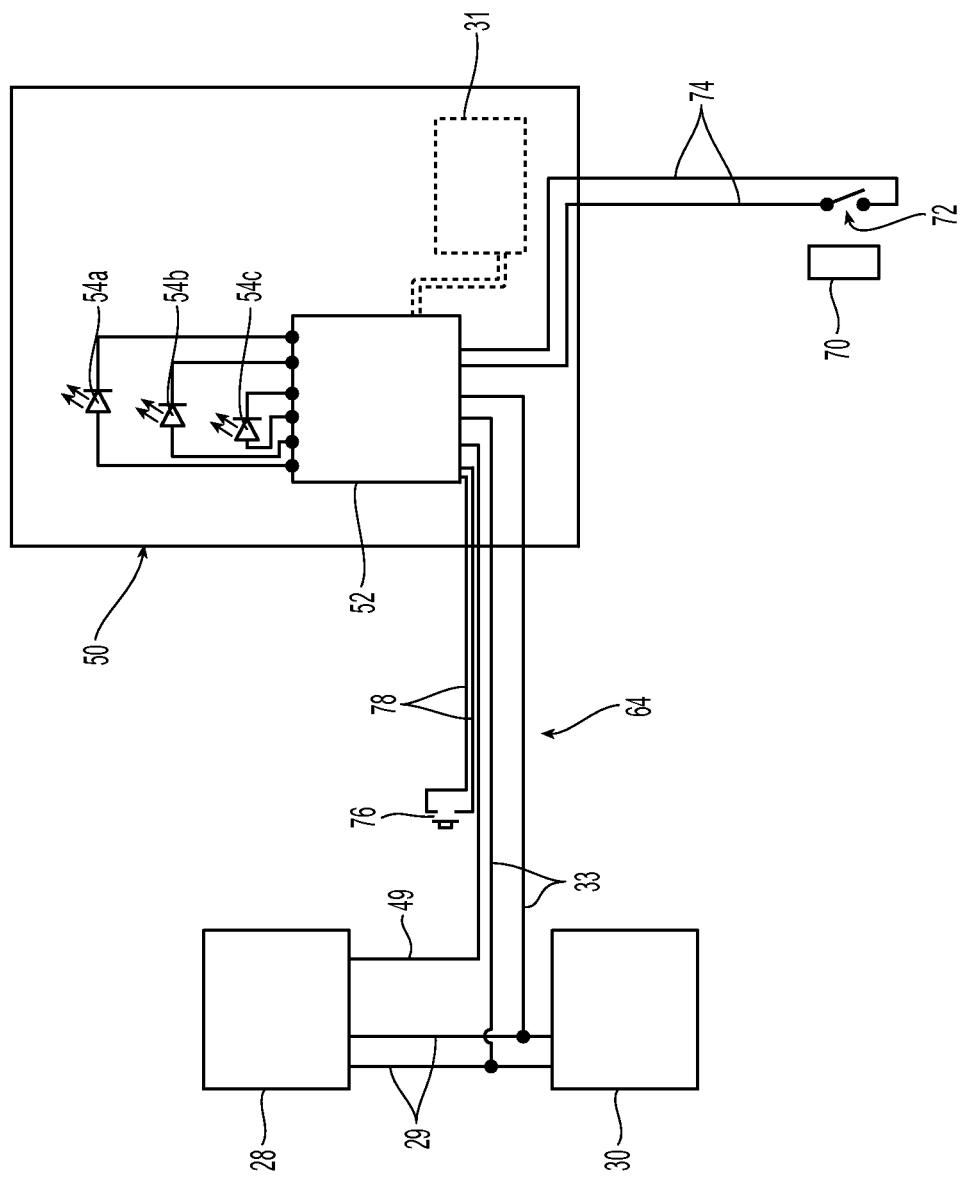
FIG. 3 is a diagrammatic view of a patient monitoring system.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

DETAILED DESCRIPTION OF THE INVENTION

A patient monitoring system 20 is shown in FIG. 1 and includes a motion detection unit 22 and a control unit 24. System 20 also includes a door sensor assembly 26 which is operably coupled with control unit 24. Motion detection unit 22 includes a motion detection sensor 28 and a removable power source 30. Motion detection sensor 28 may take the form of a passive infrared (PIR) motion detection sensor, range-controlled radar (RCR), a combination of PIR and RCR technologies or other suitable motion detection technology. Motion detection sensors employing such detection methods are commercially available. For example, a GE 45132 Choice Alert Wireless Motion Sensor commercially available from General Electric Company can be modified for use in system 20. Removable power source 30 provides the electrical power necessary to operate motion detection sensor 28 and may take the form of one or more batteries. For example, power source 30 may take the form of a nine volt battery operably coupled with sensor 28 by conductive members 29.

A first housing 32 supports both the motion detection sensor 28 and power source 30. The illustrated housing 32 allows motion detection unit 22 to be easily mounted on a wall and also includes an opening 34 for motion detection sensor 28. A cover sheet 36 which does not interfere with the operation of motion detection sensor 28 covers opening 34. As best understood with reference to FIGS. 4 and 7, the illustrated housing 32 has a back plate 38 and a front piece 40. Backplate 38 includes a keyhole opening 42 which allows housing 32 to be supported on a fastener 44 extending from the wall. System 20 may also be provided with a mounting bracket having a ball joint or other adjustable mechanism for attaching housing 32 to the wall. The ball joint allows the orientation of sensor unit 22 to be easily adjusted. Such mounting brackets are commonly used with security system sensors and are commercially available.

FIG. 7 schematically depicts one manner in which back plate 38 and front piece 40 can be secured together. As shown, an inwardly projecting lip 46 on backplate 38 is engageable with a resilient latching member 48 to snap fit the two housing parts 38, 40 together. To detach the housing parts 38, 40, front piece 40 is pressed inwardly at each location of a latching member 48 to disengage the latching members 48 from lip 46.

Although one embodiment of housing 32 for the motion detection unit 22 is shown in the drawings, various alternative embodiments of the housing may also be employed. For example, alternative mounting methods may be used instead of keyhole 42 and fastener 44. Moreover, instead of employing two separable housing parts 38, 40, two parts hinged together could be employed, or, a single housing member having a battery compartment with a removable cover plate. As a person having ordinary skill in the art will recognize, still other housing configurations may also be used with motion detection unit 22.

Control unit 24 includes a printed circuit board 50 having control circuitry 52 and at least one light source 54a-54c operably coupled with circuitry 52. Advantageously, the light source is a light emitting diode (LED) mounted on printed circuit board 50. The illustrated embodiment includes three LEDs 54a-54c mounted on printed circuit board. Printed circuit board 50 also includes digital memory 56 for storing software instructions which govern the operation of system 20. Control unit 24 may optionally include a removable power source 31, e.g., four AA batteries.

A second housing 58 supports printed circuit board 50, LEDs 54a-54c mounted on printed circuit board 50 and optional power source 31. The illustrated housing 58 includes a front piece 60 and a backplate 62. Front piece 60 includes openings 61 for LEDs 54a-54c and is detachably securable to backplate 62 using latches engageable with a lip as depicted in FIG. 7 and described above with reference to first housing 32. Backplate 62 includes keyhole openings 42 for engagement with fasteners 44 whereby housing 58 is securable to a wall surface.

Electrically conductive wiring 64 extends between the first and second housings 32, 58 and operably couples motion detection sensor 28 with control circuitry 52. Wiring 64 includes at least one wire 49 communicating control signals between circuitry and sensor 28. Wiring 64 may also include wires 33 communicating electrical current from a removable power source located in one of the housings 32, 58 to the other housing whereby batteries located in either the first housing 32 or the second housing 58 may be used to power the entire system 20. If each of the units 22, 24 are provided with their own power source, wires 33 can be omitted.

If system 20 is entirely powered by a removable power source located in only one of the housings 32, 58, it will generally be advantageous to position the power source in the motion detection unit because the detection unit consumes more power than the control unit. Alternatively, a removable power source can be positioned in both housings or system 20 could be supplied with DC electrical power with an AC/DC adaptor connectable to a conventional electrical power outlet. System 20 could also be provided with connections for both batteries and an AC/DC adaptor whereby system 20 could be powered by either batteries or a conventional power outlet.

System 20 also includes a door sensor assembly 26 which detects whether door 68 is in an open or closed condition. In the illustrated embodiment, door sensor assembly 26 includes a permanent magnet 70 mounted on door 68 and a magnetic reed switch 72. Reed switch 72 is mounted adjacent the door opening so that magnet 70 will be positioned proximate reed switch 72 when the door is closed. The depicted reed switch 72 has a conventional design which, in the absence of a magnetic field, will be in an open position. Thus, when magnet 70 is positioned at a distance from switch 72 due to door 68 being in an open condition, switch 72 will be open. When magnet 70 is positioned proximate switch 72 by closure of door 68, magnet 70 will cause reed switch 72 to close. Magnetic reed switch 72 is operably coupled with printed circuit board 50 and control circuitry 52 via wiring 74. Reed switches provide a reliable and inexpensive sensor assembly which can be used to detect whether door 68 is open or closed, however, other sensing assemblies which are capable of determining whether door 68 is open or closed may also be used with system 20.

System 20 may also include an optional manual override switch 76. Switch 76 is operably coupled with printed circuit board 50 and control circuitry 52 with wires 78 forming a part of wiring 64. Switch 76 may take the form of a push button switch, however, other types of user-input devices may also be employed. As further discussed below, when switch 76 is pressed, it will temporarily suspend normal operation of system 20. This will allow a caregiver to enter the room and interact with the patient without causing system 20 to go into an alarm status. After a predetermined time period has elapsed or other preconditions satisfied following the activation of switch 76, system 20 will return to normal operation.

It is noted that, in the illustrated system 20, override switch 76 and reed switch 72 are separate from the first and second housings 32, 58. This provides greater flexibility in the mounting of system 20. Alternative embodiments of system 20, however, may include an override switch 76 and/or a reed switch 72 that is mounted within the housing of either of the motion detection unit 22 or control unit 24. In this regard it is noted that override switch 76 can be more easily integrated into detection unit 22 or control unit 24 than reed switch 72 which must be positioned closely adjacent door 68.

As can be readily understood with reference to FIGS. 4, 5 and 7, housings 32, 58 are mounted on a wall surface 80 with wiring 64 extending between housings 32, 58. Openings are provided in the side of housings 32, 58 to allow for the entry of wiring 64 which is routed through doorway 82 and exposed, i.e., mounted exterior to wall surfaces 80 instead of being routed within the wall structure. In the illustrated embodiment, it is only the mechanical fasteners used to mount system 20 to the walls which penetrate the wall structure and all of the electrical communicating components of system 20 are mounted exterior to wall surfaces 80.

If desired, a decorative or protective sleeve or cover can be positioned over wiring 64 on the outer surface of the walls. As used herein, wiring 64 provided with such a covering would still be considered exposed so long as it was positioned exterior to wall surfaces 80 and not routed through the interior of the wall. Mounting wiring 64 on a wall in an exposed manner and routing wiring 64 through doorway 82 provides significant cost savings during the installation of system 20. Healthcare facilities often have a large number of utilities routed within the wall structures partitioning individual rooms. If a newly installed piece of equipment requires a power or data line to be routed through the interior of a wall structure, there is often a bureaucratic procedure that must be followed to prevent the installation of the new power and data lines from interfering with infrastructure already present in the wall. Such processes greatly increase the costs of installing such equipment. System 20 avoids such costs by being installable on the exterior of the walls. While such cost savings will be present in new construction, this cost savings is particularly pronounced when retrofitting an existing healthcare facility structure. It would also be possible to route wiring 64 through the wall, however, wiring 64 is a flexible cable having a plurality of wires and is intended to be routed through doorway 82.

This mounting of system 20 also has other benefits. It allows for the temporary installation of a system 20 in a patient room. For example, for a room in a ward which typically treats patients who do not present fall risks. It also allows for the relatively easy repositioning of the system components. For example, if the interior of the room is repositioned and the bed repositioned, it may be necessary or beneficial to reposition motion detection unit 22. The use of a repositionable wall mounted unit, e.g., unit 22, instead of a permanently fixed unit allows system 20 to be easily adapted to the new room configuration.

Figure 8:
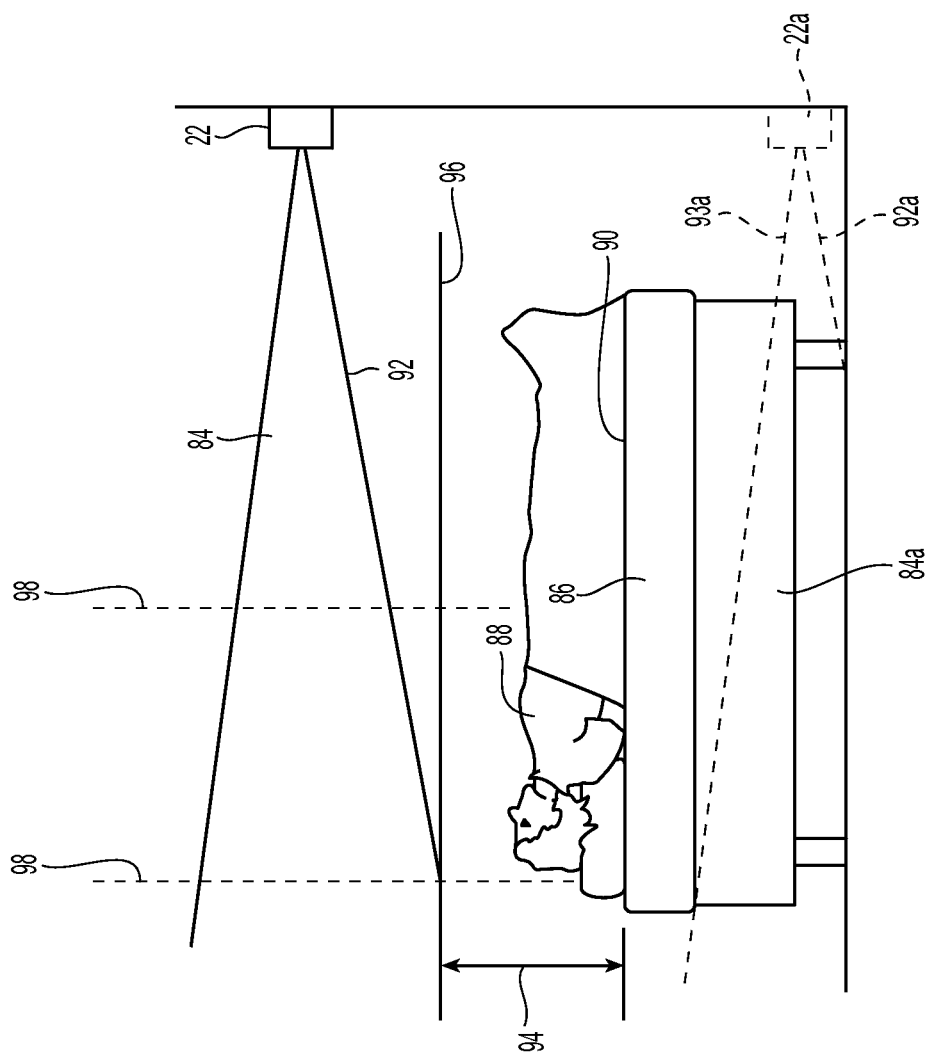
FIG. 8 is a view of a hospital room showing a detection zone.

The operation of system 20 will now be discussed. Motion detection unit 22 is mounted within the patient room 83 with motion detection sensor 28 oriented to detect movement in a detection zone 84 located above bed 86 whereby when patient 88 sits up sensor 28 will detect such movement. As best understood with reference to FIG. 8, patient 88 is located on a support surface 90 provided by bed 86 in the illustrated example. The lower boundary 92 of detection zone 84 is at least about 18 inches (45.7 cm) above support surface 90 in the area where patient 88 is located. In FIG. 8, dimension 94 is 18 inches and line 96 is 18 inches above support surface 90.

By positioning the lower boundary 85 of detection zone 84 at least about 18 inches above support surface 90, patient 88 can roll-over and otherwise reposition themselves in a prone position on bed 86 without being detected by motion sensor 28. If, however, patient 88 sits upright they will move into detection zone 84 and trigger an alarm. By positioning the lower boundary 85 of detection zone 84 at least about 18 above support surface 90, the number of false alarms, i.e., detected motion which is not indicative of the patient attempting to exit bed 86, can be reduced while still detecting motion which is indicative of patient 88 attempting to exit bed 86. In this regard, it is noted that if patient 88 is going to attempt to get out of bed 86, they will typically first sit upright with their upper torso projecting into detection zone 84 and extend their feet toward the floor. Thus, the area between dotted lines 98 above the patient's upper torso is the detection area of most concern and having lower boundary 92 positioned closely proximate a line 96 which is 18 inches above support surface 90 will generally detect motion if patient 88 exits but still allow patient 88 to reposition themselves on bed 86 without triggering a false alarm. Motion detection sensor 28 has a generally conical detection zone 84. The shape of detection zone 84, however, can be modified by the use of blinders or a shaped opening in housing 32. For example, an alternative embodiment of detection unit 22 could have a 32 with repositionable blinders which alter the dimensions of opening 34 whereby the boundaries of detection zone 84 could be adjusted.

An alternative placement of the motion detection unit is also depicted in dashed lines in FIGS. 1 and 8. In FIGS. 1 and 8, unit 22a depicts the placement of a motion detection unit relatively close to the floor. When mounted in this lowered position, the motion detection unit 22a has a detection zone 84a with a lower boundary 92a that intersects the floor surface relatively close to the unit 22a. The lower boundary 92a corresponds to the floor surface once it has intersected the floor. Unit 22a is positioned below the support surface 90 such that upper boundary 93a is below support surface 90 when it impinges upon bed 86 whereby the detection zone 84a does not include any space directly above support surface 90. When using a low mounted unit 22a, it will generally be desirable for upper boundary 93a of detection zone 84a to be no higher than support surface 90 proximate support surface 90 for the entire extent of support surface 90 as depicted in FIG. 8.

By mounting detection unit 22a below support surface 90, movement of the patient in the space above support surface 90, e.g., sitting up or rolling over, will not be detected by unit 22a or generate an alarm signal. When the patient 88 removes their feet from the bed to position them on the floor, however, their feet will intersect detection zone 84a and generate an alarm signal. It is noted that some hospital beds do not include a clear space adjacent the floor which would allow detection zone 84a to extend under and to all sides of the bed. In such situations, a second unit mounted below support surface 90 could be employed to provide the coverage desired. Alternatively, a unit 22 mounted above the support zone 90 could be used. In still other circumstances, it may be desirable to utilize motion detection units 22 that are mounted both above and below support surface 90.

Control unit 24 is mounted in hallway 83 on the opposite side of doorway 82 from sensor unit 22 with door sensor assembly 26 being mounted on and proximate door 68. Wiring 64 is routed through doorway 82 to operably couple sensor unit 22 with control unit 24.

In the illustrated embodiment, control unit 24 includes three LEDs 54a-54c but does not include any audible alarms. The absence of an audible alarm allows system 20 to be installed in a healthcare facility without increasing the noise level of the facility. Various different means may be used to signal an alarm event and current status of system 20. In the illustrated embodiment, LED 54a is a green light and illumination of LED 54a indicates that system 20 is active and no movement has been detected. LED 54b is a red light and illumination of LED 54b indicates that motion has been detected. LED 54c is an amber light and illumination of LED 54c indicates that system 20 is inactive. In operation, system 20 will typically be used with fall-risk patients and illumination of LED 54b will alert caregivers that the patient is attempting to leave the bed and that a caregiver should check on the patient to provide assistance and limit the potential for an injury-causing fall.

Control circuitry 52 is configured to illuminate LED 54b when motion detector 28 senses movement and door sensor assembly 26 detects that door 68 is closed. LED 54b may be kept illuminated only during the time period during which such movement is detected, or, it may remain illuminated for a predetermined time period, e.g., 5 or 10 minutes, after detecting motion with door 68 in a closed condition. Alternatively, LED 54b may be kept illuminated until door 68 is opened. Still another option is to keep LED 54b illuminated until both the expiration of a predetermined time period and the opening of door 68 occurs. If system 20 includes an override switch 76, another option is to retain LED 54b in an illuminated condition until override switch 76 is activated.

As mentioned above, the purpose of illuminating LED 54b is to alert a caregiver that patient 88 has moved and may be exiting bed 86. The preferred method of terminating the alert provided by LED 54b may depend, in part, on the physical layout, staffing and procedures of the healthcare facility in which system 20 is installed.

As mentioned above, control circuitry 52 illuminates LED 54a when system 20 is active and door 68 is in a closed condition and motion sensor 28 has not detected movement. If door 68 is opened, control circuitry 52 will illuminate LED 54c to indicate that system 20 is inactive and will also prevent the illumination of LED 54b. This will allow a caregiver to enter the room leaving door 68 in an open condition, attend to patient 88, and then leave the room closing the door, without causing system 20 to go into an alarm condition, i.e., illuminate LED 54b, while the caregiver is in the room attending to patient 88.

While many tasks required of a caregiver can be performed with door 68 in an open condition and without privacy concerns, it will be preferable to close door 68 for some caretaker tasks for reasons of patient privacy. System 20 may optionally include an override switch 76 for such situations. If an override switch 76 is provided, the caregiver can enter the room, activate switch 76, close door 68 and then attend to the care of patient 88 without causing an alarm condition. Activation of switch 76 will cause system 20 to illuminate LED 54c and prevent the illumination of LED 54b until certain preconditions have been met or a predetermined time period has elapsed even though movement is being detected by sensor 28 and door 68 is closed.

System 20 can be provided with a switch 76 on either side of door 68. When switch 76 is located on the same side of door 68 as motion detection unit 22, activation of switch 76 advantageously places system 20 in an inactive condition until door 68 is opened and once again closed indicative of the care giver leaving the room. As previously mentioned, an alternative approach would be for activation of switch 76 to place system 20 in an inactive condition for a predetermined period of time, e.g., five or ten minutes. Various other embodiments of system 20 could utilize other preconditions for determining when to return system 20 to normal operation.

While the illustrated embodiment includes three LEDs 54a-54c, alternative embodiments of system 20 may utilize control units having a different number of light sources. For example, LED 54c could be omitted from system 20 and the absence of any lighted LED on the control unit would be used to indicate that system 20 was in an inactive state. Alternatively, if only two lights were provided, it could be LED 54a that is omitted with the absence of any illuminated light indicating that the system is operating and is not detecting movement. Still other variations of illuminated elements could be employed to communicate the status of the system.

With regard to such variations, it is noted that the embodiment described above includes an LED 54b that has an alarm condition which indicates that the door is closed and motion is detected and a non-alarm condition which are indicated by selective illumination of LED 54b. In the described embodiment, the alarm condition is indicated by illumination of LED 54b and the non-alarm condition is indicated by the non-illumination of LED 54b. It will generally be desirable to indicate the alarm condition by illumination of LED 54b, however, it would be possible to indicate the alarm condition by non-illumination and the non-alarm condition. It would also be possible for a single LED light to indicate multiple non-alarm conditions. For example, continuous illumination of a light could indicate an alarm condition, non-illumination of the same light could indicate that the system was operating normally without detecting patient movement and slow blinking of the light could indicate that the battery was low or that the system had been temporarily suspended from normal operation by activation of the override switch.

As can be understood from the foregoing discussion, system 20 is well-adapted for use in health-care facilities having a closed door policy wherein the doors of patient rooms are kept closed unless another person is present in the room with the patient. Such policies are generally intended to shield patients from excessive noise and the lack of an audible alarm on system 20 also facilitates the operation of such care facilities. In this regard it is noted that LED 54b is the sole alarm or alert communication element of system 20. Alternative embodiments of system 20, however, could include wireless transmitter to communicate alarms and other status information to a central base unit. For example, wireless base units which are designed for communication with multiple motion sensor units similar to units 22 are commercially available from General Electric Company. The wireless communications may be transmitted using ZigBee or other suitable protocols.

Figure 9:
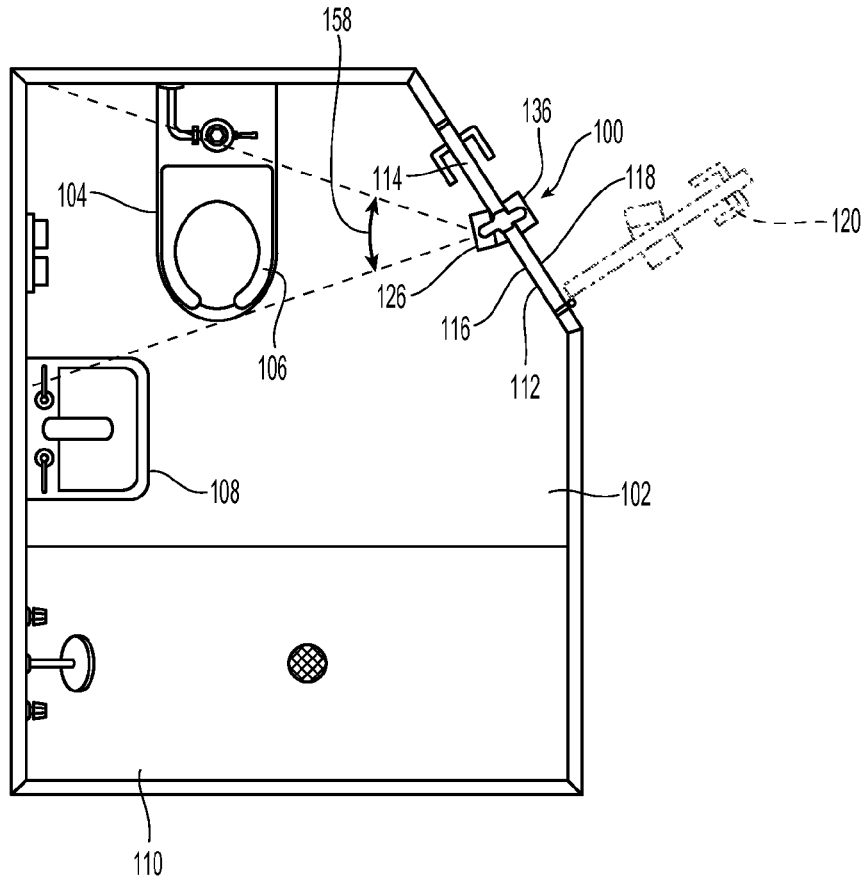
FIG. 9 is a plan view of a healthcare facility bathroom.
Figure 10:
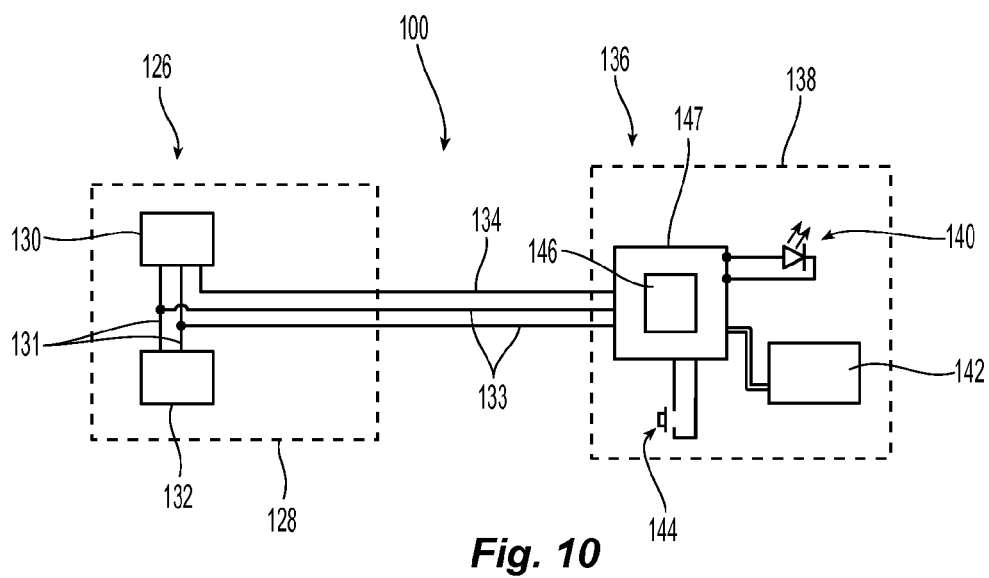
FIG. 10 is a schematic diagram of a monitoring system for use in a bathroom setting.
Figure 11:
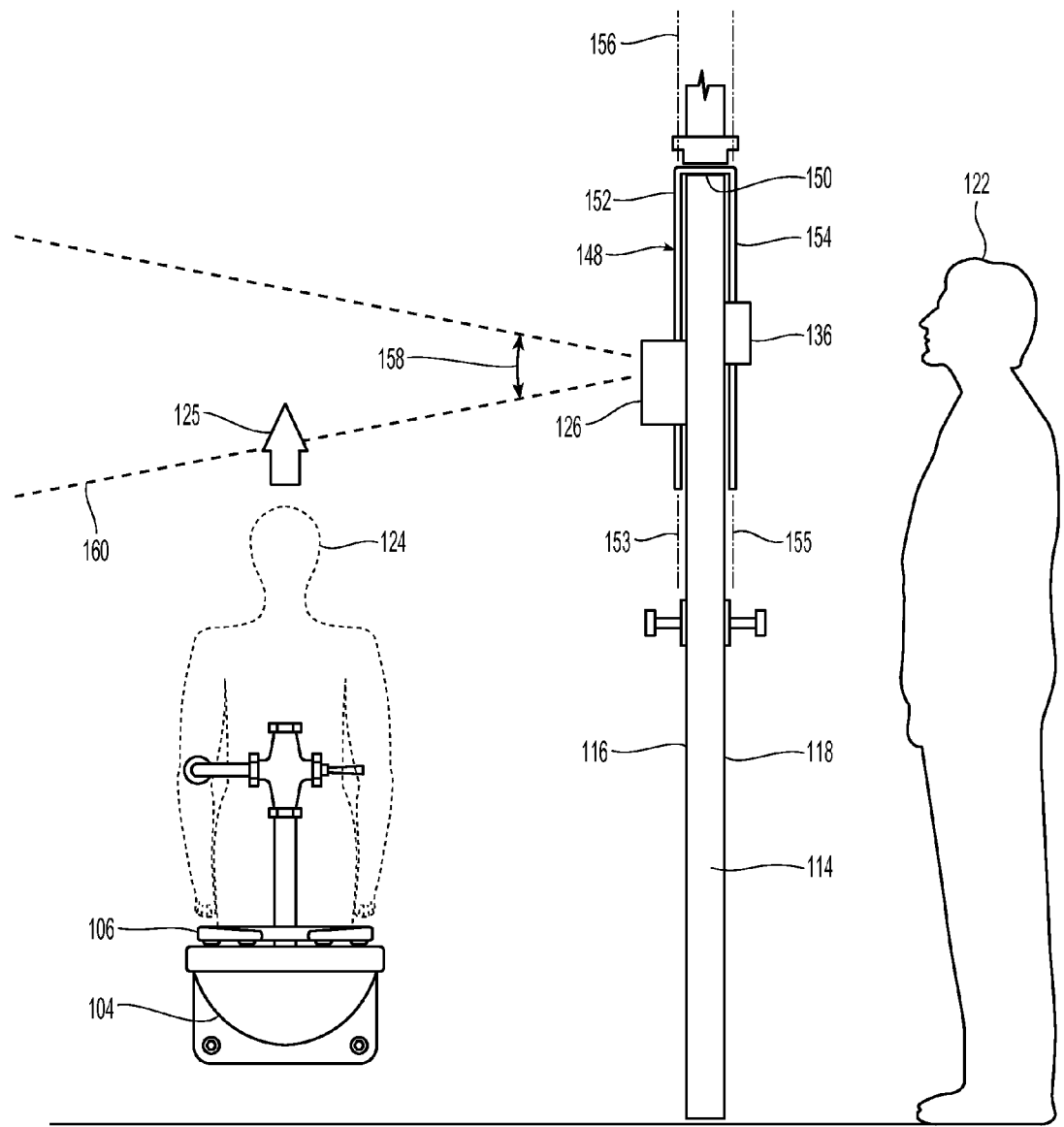
FIG. 11 is a side view of the bathroom monitoring system after installation.

FIGS. 9-11 provide an overview of a patient monitoring system 100 for monitoring a patient in a bathroom 102 having a toilet 104. The illustrated toilet 104 has a conventional toilet seat 106. The illustrated bathroom 102 is representative of a typical bathroom found in a healthcare facility and includes a sink 108 and handicap accessible shower 110. Not shown are hand rails which are located along majority of the wall surfaces. A conventional door 114 is mounted on hinges and is moveably disposed within a doorway 112. Doorway 112 provides access to the bathroom when door is in an open position and the door blocks access through the doorway when the door is in a closed position. When door 114 is closed, interior surface 116 of door 114 faces into the bathroom 102 and an oppositely disposed exterior surface 118 faces away from the bathroom 102. FIG. 9 shows door 114 in the closed position in solid lines while dashed lines 120 show door 114 in the open position.

FIG. 11 depicts door 114 in a closed position with a caregiver 122 standing outside bathroom 102 waiting to assist fall-risk patient 124 return to a standing position. As will be evident from the discussion that follows, system 100 alerts caregiver 122 standing outside closed door 114 if fall-risk patient 124 attempts to rise from toilet 104 without first requesting assistance from caregiver 122. If patient 124 attempts to stand without assistance, caregiver 122 can step into bathroom 102 to provide assistance and thereby help prevent a potential fall by patient 124.

FIG. 10 provides a schematic diagram of system 100. Motion detection unit 126 is very similar to motion detection unit 22 described above. Similar to unit 22 it has a housing 128 within which a motion detection sensor 130 is disposed. Sensor 130 is identical to sensor 28. The illustrated housing 128 which supports sensor 130 is nearly identical to housing 32 with the only distinctions being found in the backplate of the housing. Those distinctions include the location where wiring exits the housing and the method of attaching the housing to a supporting structure. Similar unit 22, motion detection unit 126 may include a removable power source 132 which provides the electrical power necessary to operate motion detection sensor 130 and may take the form of one or more batteries. For example, power source 132 may take the form of a nine volt battery operably coupled with sensor 130 by conductive members 131.

Alarm unit 136 is also schematically depicted in FIG. 10 and includes a housing 136 which supports an alarm device 140, a removable power source 142 and a switch 144. Control circuitry 146 is also disposed in housing 136 in the illustrated embodiment.

Control circuitry 146 is located on printed circuit board 147 and operably couples motion detection sensor 130 with alarm device 140. Printed circuit board 147 includes digital memory for storing software instructions which govern the operation of system 100 which is configured to activate alarm device 140 when motion detection sensor 130 detects motion.

In the illustrated embodiment, alarm device 140 is a light emitting diode (LED) and this LED is the sole alarm communication device. Alternative embodiments might also include an alarm device which is capable of making an audible noise or include both a light and an audible alarm device to communicate an alarm event. Removable power source 142 may take the form of four AA batteries.

A manually operated switch 144 is also supported on housing 138 and operably coupled with the control circuit 146. Switch 144 is used to activate and de-activate the entire system 100. In this regard, it is noted that because switch 144 is in communication with control circuitry 146, it is also operably coupled with motion detection sensor 130. Switch 146 is also operably coupled with alarm device 140 via control circuitry 146. Thus, when switch 146 is pressed, it will selectively activate or de-activate control circuitry 146, alarm device 140 and motion detection sensor 130.

Although switch 144 is mounted on the alarm unit housing 136 in the illustrated embodiment, it could alternatively be mounted on housing 128 or in a housing separate from both motion detection unit 126 and alarm unit 136. Alarm unit housing 136, however, provides a convenient location for switch 144 and allows caregiver 122 to easily turn on system 100 when accompanying a patient to the bathroom and turn the system off when leaving.

The ability to turn off both motion detection unit 126 and alarm unit 136 with a single switch 144 makes it convenient to turn the system on and off and thereby facilitates turning the system on only when it is in use. This will, in turn, prolong the life of removable power sources 132, 142 which are respectively located in housings 128, 138.

Because the use of switch 144 will prolong battery life, each of housings 128, 138 can conveniently include a removable power source. It would also be possible to utilize a single removable power source located in only one of the housings 128, 138 to power the entire system. In such an embodiment, wires 133 can communicate electrical power between units 126, 136. It would also be possible to use an electrical power cord plugged into an outlet to power one or both units 126, 136. Because system 100 is mounted on a moveable door, the use of a power cord will generally not be desirable. If each of the units are provided with their own power source, wires 133 can be omitted.

Electrically conductive communication wiring 134 extends between the first and second housings and operably couples motion detection sensor with control circuitry. Wiring 134 communicates control and data signals between motion detection unit 126 and alarm unit 136. For example, when motion detection sensor 130 detects movement, this will be communicated to alarm unit 136 via wiring 134. Alternatively, a wireless form of communication could be employed. The use of a wired system, however, will provide cost savings and reduce power consumption.

LED 140 can be used to communicate when power source 142 is low. For example, LED 140 can be illuminated steadily to indicate an alarm event and flash to indicate that power source 142 is low. To indicate when power source 132 is low, a separate LED can be provided on motion detection unit 126 or this information could be communicated to control circuitry 146 which would then communicate this information using LED 140. Alternatively, alarm unit 136 could include multiple LEDs. For example, three LEDs could be used with one LED indicating an alarm event, a separate LED indicating a low power source in alarm unit 126 and the third LED indicating that motion detection unit 126 has a power source running low. Various other communication systems could alternatively be employed with system 100.

Support structure 148 is used to removeably mount system 100 on door 114 and supports motion detection unit 126 and alarm unit 136 on opposite sides of door 114. It supports housing 128 of unit 126 proximate the interior surface 116 of door 114 and housing 138 of unit 136 proximate exterior surface 118 of door 114. This allows motion detection unit 126 to monitor patient 124 inside bathroom 102 with door 114 closed, while caregiver 122 watches alarm unit 136 outside bathroom 102.

In the illustrated embodiment, support structure 148 has a central portion 150 that extends over and engages top edge 115 of door to thereby mount support structure 148 on door 114. While the illustrated support structure 148 hangs on the top edge 115 of door 114 other embodiments could also be employed. For example, a clamping mechanism could be used to clamp onto the door either proximate the top edge or one of the side edges to removeably secure support structure on door 114.

Because support structure 148 merely hangs on door 114, it is easily installed and also easily removed from door 114. This allows system 100 to be moved from room to room to be used with patients that present a fall-risk without having to have a system 100 installed on all of the bathroom doors in a healthcare facility.

Support structure 148 includes two elongate members 152, 154 that extend from opposite sides of central portion 150. First elongate member 152 extends from the interior side of central portion 150 and is positioned proximate interior surface 116 of door 114 and supports housing 128 of motion detection unit 126. Second elongate member 154 extends from exterior side of central portion 150 and is positioned proximate exterior surface 118 of door 114 and supports housing 138 of alarm unit 136.

Figure 12:
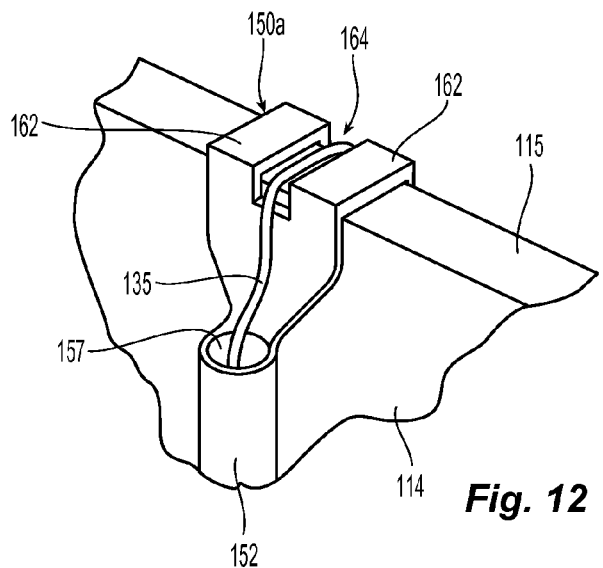
FIG. 12 is a partial perspective view of one embodiment of the bathroom monitoring system showing how it can be mounted on a door.
Figure 13:
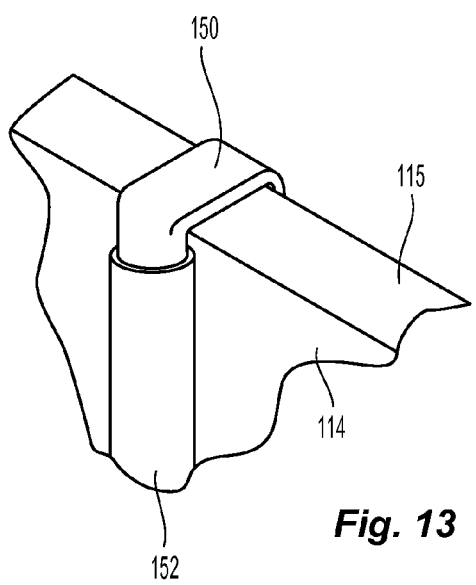
FIG. 13 is a partial perspective view of another embodiment of the bathroom monitoring system showing an alternative method of mounting the system on a door.

FIGS. 12 and 13 show two alternative embodiments of the central portion of support structure 148. In each of these embodiments, wiring 135 extends between motion detection unit 126 and alarm unit 136 over the top edge 115 of door 114. In the embodiment of FIG. 12, central portion 150a has two thin flat sections 162 separated by a void 164. Wiring 135 extends over top edge 115 of door 114 in the void 164 between sections 162. Central portion 150a depicted in FIG. 12 provides a low profile that facilitates the closure of door 114 while support structure 148 is installed thereon.

It is noted that wiring 135 collectively includes communication lines 134 and power lines 133 (if present) that extend between units 126, 136. It would also be possible to have units 126 and 136 communicate wirelessly and eliminate all wiring extending between the two units. The use of wiring, however, reduces potential interference with other healthcare equipment and reduces the cost of the system.

Central portion 150 depicted in FIG. 13 takes the form of a hollow tubular member that has a generally flattened, but still tubular, section that extends over the top edge 115 of door 114. Wiring 135 extends through the hollow interior of central portion 150 over the top edge 115 of door 114 in the embodiment of FIG. 13. The embodiment of FIG. 13 has a slightly greater height than the embodiment of FIG. 12 but fully encloses wiring 135 as it extends over top edge 115.

When wiring 135 is extended between units 126, 136 it is not necessary for elongate members 152, 154 to have hollow interiors for running wires 135, however, it will generally be advantageous and more aesthetically pleasing to for each of the elongate members 152, 154 to define a hollow interior 157 for routing wiring 135 at least part of the distance between housings 128, 138.

Central portion 150, 150a and elongate members 152, 154 may be formed out of a polymeric material. Elongate members 152, 154 are advantageously formed out of conventional rigid plastic tubing to reduce manufacturing costs. Elongate members 152, 154 may be joined with central portion 150, 150a using adhesives, welding or other suitable means. For example, central portion 150 might include a socket into which the end of members 152, 154 are inserted and attached using an adhesive. Alternatively, central portion 150, 150a might have a smaller diameter portion that is inserted into members 152, 154. In still other embodiments, members 152, 154 might be formed integrally with central portion 150 whereby support structure 148 is a monolithic structure.

Elongate member 152 defines an axis 153 and housing 128 is axially repositionable on elongate member 152. In other words, it is possible to adjust the vertical position of housing 128 on elongate member 152. This allows the motion detection unit 126 to be adjusted to properly position detection zone 158 above toilet 104 as further discussed below. Because not all bathrooms have the same layout, it is also desirable to have the ability to adjust the angular position of detection zone 158. This can be accomplished by angularly repositioning housing 128 about a yaw axis 156 that is substantially parallel to axis 153. In the illustrated embodiment, yaw axis 156 extends vertically and coincides with axis 153.

Figure 15:
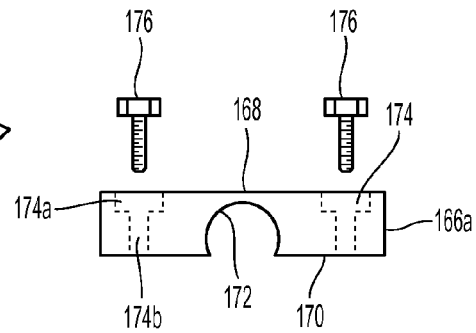
FIG. 15 is an exploded top view of a shim member for the motion detection unit.
Figure 16:
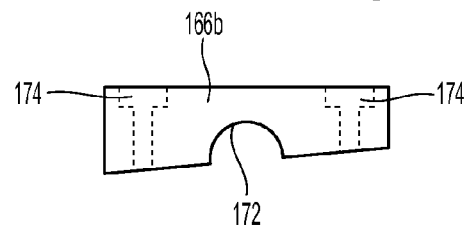
FIG. 16 is a top view of a second shim member.
Figure 17:
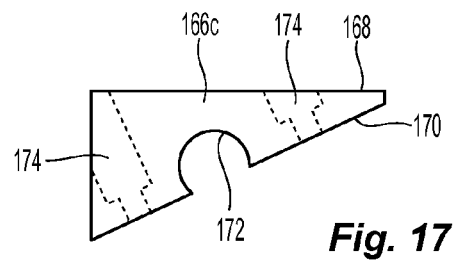
FIG. 17 is a top view of a third shim member.
Figure 14:
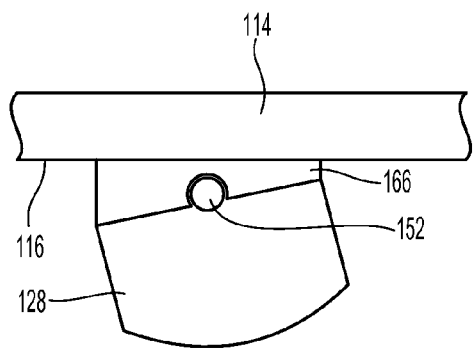
FIG. 14 is a top view of the motion detection unit of a bathroom monitoring system.
Figure 18:
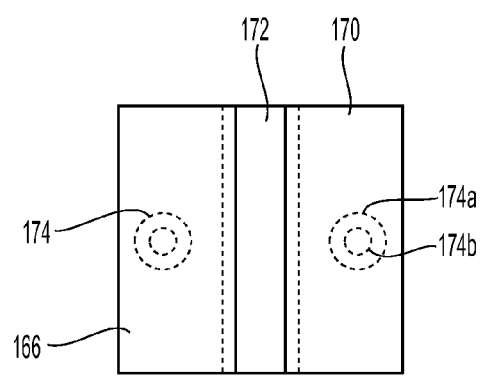
FIG. 18 is a front view of the shim member of FIG. 15.

FIGS. 14-18 illustrate one manner in which housing 128 can be angularly repositioned about yaw axis 152 using shim members 166. By providing system 100 with a plurality of shim members 166a-166c which are selectively attachable to housing 128, the appropriate shim member can be positioned between housing 128 and interior surface 116 of door 114 to position housing 128 in an appropriate angular position about the yaw axis 156 so that detection zone 158 is positioned above the toilet 104. As can be seen in FIGS. 15-17, each of the plurality of shim members 166a-166c have a different configuration whereby shim members 166a-166c each define a different angular position for housing 128 about yaw axis 156.

Each of the shims 166a-166c have a back surface 168 that engages interior door surface 116 and a front surface 170 that engages the back of housing 128. Housing 128 includes a front section 178 and a rear section 180 which may joined together in a suitable manner such as described above with regard to other housing assemblies. Advantageously, housing sections 178 and 180 can be easily separated and re-attached to permit the convenient changing of power source 132 which may take the form of a battery. Front section 178 includes an opening 182 through which motion detection sensor 130 monitors the surrounding environment. The rear surface of housing 128 is shown in FIG. 23 and includes two threaded openings 184. Openings 184 facilitate the attachment of a shim member 166 to rear housing section 178.

Shim members 166a-166c each include two counterbore openings 174 having a large diameter section 174a and a small diameter section 174b. Threaded fasteners 176 are inserted through counterbores 174 to engage openings 184 in housing 128 to thereby attach a selected one of the shim members 166a-166c to housing 128. The head of threaded fastener 176 will be seated within large diameter section 174a so that it does not engage and scratch door 114. When attaching a shim member to housing 128, channel 172 receives elongate member 152. Counterbores 174 extend perpendicular to front surface 170 of the shim members.

A slot 186 in elongate member 152 allows wiring 135 to pass from the back of housing 128 into the hollow interior 157 of member 152. Slot 186 also allows for the vertical adjustment of housing 128 on member 152. Housing 128 could be secured in the desired vertical position by dimensioning shim members 166a-166c so that when fasteners 176 are tightened, the shim member will clamp elongate member 152 between the shim member and the rear of housing 128 to secure housing 128 in place. The illustrated embodiment does not, however, employ this method, instead a stop member is secured to elongate member 152 below housing 128 to hold housing 128 in the desired location.

FIG. 21 illustrates one embodiment of a stop member. Stop member 190 illustrated in FIG. 21 includes two ring portions 192 which are joined by a resilient hinge portion 194. Stop member 190 may be formed out of a metal or suitably strong and resilient plastic material. Ring portions 192 each define a central opening 196 through which elongate member 152 can be inserted.

By pressing ring portions 192 towards each other, central openings 196 will become sufficiently aligned to allow clip 190 to be repositioned on member 152. When ring portions 192 are released, hinge section 194 will bias rings 192 away from each other whereby they will firmly engage member 152 holding stop member 190 securely in place. Stop member 190 can thereby support housing 128 on member 152 while allowing for the convenient vertical repositioning of housing 128 on member 152.

It is noted that elongate member 152 may advantageously include markings 188 that can be used to when repositioning housing 128. For example, it may be desirable to reposition housing 128 when a particularly tall or short patient uses the bathroom and markings 188 can facilitate the movement of housing 128 when undertaking such adjustments.

An alternative stop member 198 is depicted in FIG. 22 and can be used instead of clip 190. Stop member 198 includes a ring 200 that slides on member 152. Ring 200 includes a threaded passage through which set screw 202 extends. By engaging and disengaging set screw with member 152, ring 200 can be repositioned on member 152 to thereby reposition housing 128.

FIG. 24 illustrates an alternative to shim members 166a-166c for adjusting the angular position of housing 128. Shown in FIG. 24 is a threaded adjustment member 204 which is threaded into one of openings 184 on the back of housing 128. A elastomeric foot 206 is positioned on the head of member 204. Foot 206 engages interior surface 116 of door 114 and prevents scratching of door 114. A pocket 208 on foot 206 receives the head of member 204. Only one adjustment member 204 is attached to housing 128 and by adjusting the depth to which member 204 is inserted into opening 184 the angle at which member 204 will bias housing 128 relative to door 114 about yaw axis 156 can be adjusted.

While different methods of adjusting the vertical and angular position of housing 128 have been illustrated and described, still other variations may also be employed with housing 128. Moreover, housing 128 can also vary from the illustrated embodiment.

Figure 25:
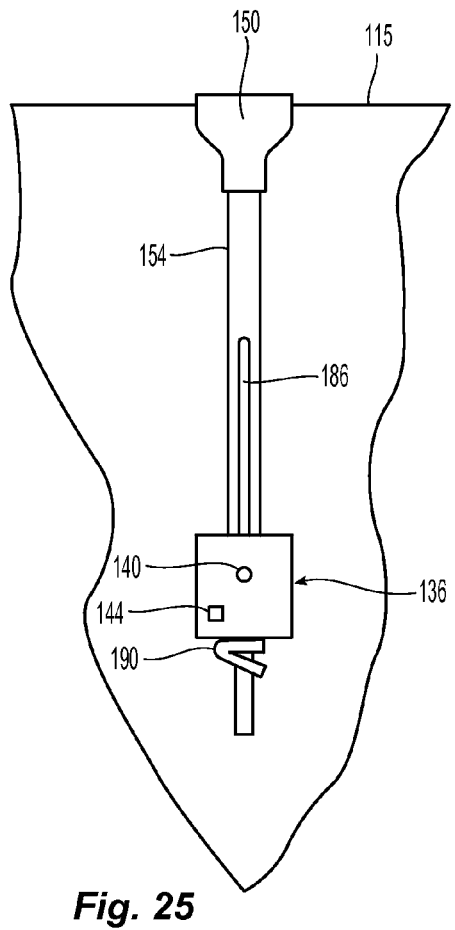
FIG. 25 is a frontal view of the alarm unit and support structure mounted on a door from outside the bathroom.
Figure 26:
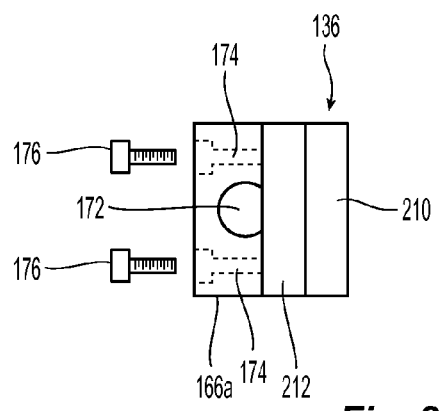
FIG. 26 is a top exploded view of the alarm unit.

Alarm unit 136 is mounted on elongate member 154 which defines an axis 155. Housing 138 of unit 136 can be axially repositioned on member 154 using a clip 190 or stop member 198 similar to that discussed above. The use of a clip 190 with alarm unit 136 is shown in FIG. 25. As can be seen in FIG. 25, elongate member 154 can include a slot 186 to allow cables to pass from the hollow interior of member 154 to the back of unit 136 while still providing for the vertical adjustment of unit 136. FIG. 26 illustrates how a shim unit 166a can be used to attach unit 136 to member 154. Shim unit 166a positions the front of unit 136 substantially parallel with the exterior door surface 118. Similar to housing 128, housing 138 of unit 136 includes a front section 210 and a rear section 212 which are detachably secured together. Rear section 212 includes threaded openings for engaging fasteners 176.

Figure 27:
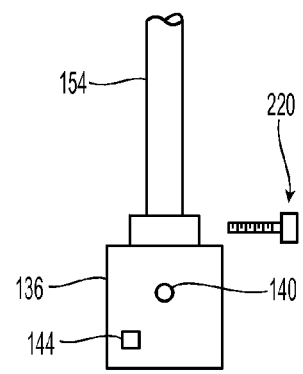
FIG. 27 is a front exploded view of the alarm unit depicting one means for attaching the alarm unit to the support structure.
Figure 28:
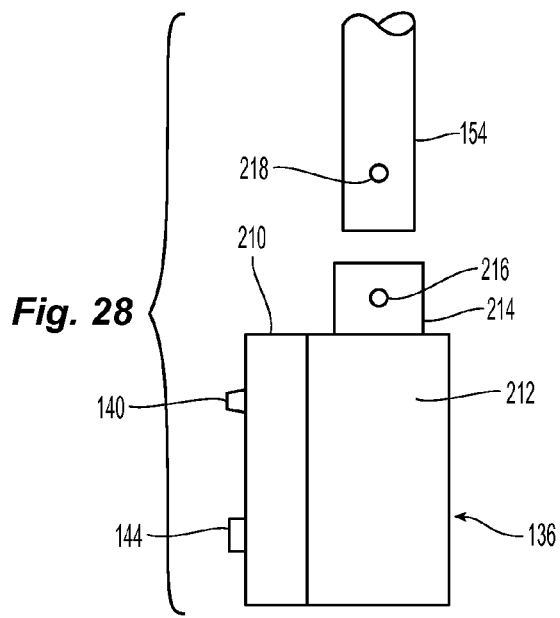
FIG. 28 is an exploded side view of the alarm unit and support structure of FIG. 27.

As a general rule it will be desirable to position alarm unit at about eye-level for an adult to allow a caregiver to easily reach switch 144 and see alarm device 140. As a result, significant leeway exists for the vertical positioning of alarm unit 136 and it is not necessary for alarm unit to be axially repositionable on elongate member 154. FIGS. 27 and 28 illustrate an alarm unit 136 having a housing 138 with a predefined installation position on elongate member 154. In other words, housing 138 has a single attachment location on member 154 and it is not adapted to be repositioned on member 154.

More specifically, in the embodiment of FIGS. 27 and 28, the rear section 212 of housing 138 includes a socket 214 which receives the lower end of elongate member 154 to thereby secure housing 138 to member 154. In the illustrated embodiment, socket 216 includes a threaded opening that is aligned with opening 218 in member 154. A threaded fastener 220 is secured in opening 216 and extends into opening 218 to secure housing 136 on member 154. Alternative methods of securing member 154 to housing 138 may also be employed.

The use of system 100 will now be described. System 100 is mounted on door 114 with motion detection unit 126 on interior surface 116 of door 114 and alarm unit 136 on exterior surface 118. The vertical position of motion detection unit 126, and thus motion detection sensor 130, is then adjusted so that the lower boundary 160 of the detection zone 158 defined by sensor 130 is positioned roughly about 42 inches over the seating surface at the center of toilet 104 when an adult of typical height is the anticipated patient. This distance above the seating surface may need to be adjusted depending on the height of the patient. Because the geometry of detection zone 158 will be known in advance, system 100 can be provided with a chart indicating the geometry of detection zone 158 so that the vertical position of housing 128 necessary to obtain the desired height of lower boundary 160 above the seating surface can be determined by measuring the horizontal distance from the center of the toilet to the location of housing 128.

The angular position of housing 128 and thus motion detection sensor 130 about yaw axis 156 is then adjusted so that sensor 130 is pointed in the direction of toilet 104 and detection zone 158 extends over toilet 104.

The height of lower boundary 160 above toilet 104 is selected so that a patient 124 seated on the toilet will be located below lower boundary 160 without intruding into detection zone 158. Lower boundary 160 is low enough, however, so that when the patient rises from the toilet seat, the patient will enter the detection zone 158. When patient 124 enters detection zone 158 and is detected by sensor 130, this will be communicated to control circuitry 146 which will, in turn, activate alarm device 140. Activation of alarm device 140 may take the form of lighting an LED. Arrow 125 in FIG. 11 schematically represents patient 124 rising from toilet 104 and entering detection zone 158.

As discussed above, many fall-risk patients suffer falls attempting to rise from a toilet unassisted. Such patients may attempt to stand without assistance even though they have been instructed to ask for assistance and a caregiver is standing immediately outside the door waiting to assist the patient. When system 100 is in use, if a patient attempts to rise from the toilet without asking for assistance, a caregiver 122 located outside door 114 will be notified by the activation of alarm device 140 that patient 124 is attempting to stand. This will give caregiver 122 the opportunity to step into bathroom 102 to assist patient 124 as patient 124 rises from toilet 104.

Switch 144 allows the caregiver 122 to selectively activate and deactivate system 100. This allows system 100 to be activated only when a patient is using bathroom 102 to thereby prolong the useful life of power sources 132, 142.

Control circuitry 146 may also be programmed to automatically deactivate system 100 after a predetermined time period has elapsed after activating system 100. For example, system 100 may be automatically deactivated 20 minutes or other suitable time period after activation. Automatic deactivation of system 100 will ensure that system 100 does not remain activated and drain the reserves of power sources 132, 142 if a caregiver forgets to deactivate system 100 after assisting a patient 124.

Switch 144 can be located on either unit 126, 136 or at another location. It will generally be most convenient, however, to locate switch 144 on alarm unit 136. This will allow caregiver 122 to initially activate system 100 from outside bathroom 102 when first arriving at bathroom 102 with patient or after assisting patient 124 sit on toilet 104, exiting bathroom 102 and closing door 114. For example, if caregiver 122 forgets to activate system 100 when first arriving at the bathroom with the patient, caregiver 122 can activate system 100 after assisting the patient sit on toilet 104 and exiting bathroom 102 without having to reenter bathroom 102.

While this invention has been described as having an exemplary design, the present invention may be further modified within the spirit and scope of this disclosure. This application is therefore intended to cover any variations, uses, or adaptations of the invention using its general principles.

What is claimed is:

1. A patient monitoring system adapted for use with a bathroom having a toilet wherein a doorway provides entry into the bathroom and a door is moveably mounted in the doorway and wherein, when the door is in a closed position, the door has an interior surface facing into the bathroom and an opposing exterior surface facing away from the bathroom, the system comprising:
  a motion detection unit including a motion detection sensor and a first housing supporting the motion detection sensor;
  an alarm unit having an alarm device and a second housing supporting the alarm device;
  control circuitry operably coupling the motion detection sensor with the alarm device, the control circuitry configured to activate the alarm device when the motion detection sensor detects motion; and
  a support structure removably supportable on the door wherein the support structure is adapted to support the first housing proximate the interior surface of the door and support the second housing proximate the exterior surface of the door.

2. The system of claim 1 wherein the support structure has an engagement portion adapted to extend over and engage a top edge of the door and thereby mount the support structure on the door.

3. The system of claim 2 wherein the support structure further comprises first and second elongate members extending from opposite sides of the engagement portion whereby the first elongate member is positioned proximate the interior surface of the door and the second elongate member is positioned proximate the exterior surface of the door when the support structure is mounted on the door, the first housing being supported on the first elongate member and the second housing being supported on the second elongate member.

4. The system of claim 3 wherein the first elongate member defines a first axis and the first housing is axially repositionable on the first elongate member.

5. The system of claim 4 wherein the first housing is angularly repositionable about a yaw axis substantially parallel to the first axis.

6. The system of claim 4 wherein the second elongate member defines a second axis and the second housing is axially repositionable on the second elongate member.

7. The system of claim 4 wherein the second housing has a predefined installation position on the second elongate member.

8. The system of claim 3 wherein wiring extends between the first and second housings and the first and second elongate members each define a hollow interior for routing the wiring at least part of the distance between the first and second housings.

9. The system of claim 1 wherein the alarm unit further comprises a manually operated switch operably coupled with the control circuitry, the switch selectively activating and de-activating the system.

10. The system of claim 9 wherein the control circuitry is disposed in the second housing and each of the first and second housings have a removeable power source, the removable power source in the first housing powering the motion control sensor and the power source in the second housing powering the control circuitry and the alarm device.

11. The system of claim 10 wherein the alarm device is an LED light and the LED light is the sole alarm communication device.

12. A patient monitoring system adapted for use with a bathroom having a toilet wherein a doorway provides entry into the bathroom and a door is moveably mounted in the doorway and wherein, when the door is in a closed position, the door has an interior surface facing into the bathroom and an opposing exterior surface facing away from the bathroom, the system comprising:
  a motion detection unit including a motion detection sensor and a first housing supporting the motion detection sensor;
  an alarm unit having an alarm device and a second housing supporting the alarm device;
  control circuitry operably coupling the motion detection sensor with the alarm device, the control circuitry configured to activate the alarm device when the motion detection sensor detects motion;
  a manually operated switch supported on the second housing, the switch being operably coupled with the motion detection sensor and the control circuitry wherein the switch selectively activates and deactivates the system; and
  a support structure removably supportable on the door, the support structure including an engagement portion adapted to extend over and engage a top edge of the door and thereby mount the support structure on the door, the support structure further including first and second elongate members extending from opposite sides of the engagement portion whereby the first elongate member is positionable proximate the interior surface of the door and the second elongate member is positionable proximate the exterior surface of the door when the support structure is mounted on the door, the first housing being supportable on the first elongate member proximate the interior surface of the door and the second housing being supportable on the second elongate member proximate the exterior surface of the door, wherein the first elongate member defines a first axis and the first housing is axially repositionable on the first elongate member and wherein the first housing is angularly repositionable on the first elongate member about a yaw axis substantially parallel to the first axis; and
  wherein the motion detection sensor defines a detection zone, the motion detection sensor being positionable to extend the detection zone over the toilet whereby a patient seated on the toilet will be located below the detection zone without intruding into the detection zone, and, when the patient rises from the toilet, the patient will enter the detection zone thereby activating the alarm device whereby a caregiver positioned outside the bathroom proximate the door with the door in the closed position will be notified by the alarm device.

13. The system of claim 12 wherein the control circuitry is disposed in the second housing and each of the first and second housings have a removeable power source, the removable power source in the first housing powering the motion control sensor and the power source in the second housing powering the control circuitry and the alarm device, wherein the alarm device is an LED light, and wherein wiring extends between the first and second housings and the first and second elongate members each define a hollow interior for routing the wiring at least part of the distance between the first and second housings.

14. The system of claim 12 further comprising a plurality of shim members selectively attachable to the first housing and positionable between the first housing the interior surface of the door to thereby define an angular position of first housing about the yaw axis, each of the plurality of shim members having a different configuration whereby each of the plurality of shim members defines a different angular position for the first housing about the yaw axis.

15. A method of monitoring a patient in a bathroom having a toilet wherein a door is moveably mounted in a doorway, the doorway providing access to the bathroom when the door is in an open position and the door blocks access through the doorway when the door is in a closed position, and wherein, when the door is in the closed position, the door has an interior surface facing the bathroom and an exterior surface facing away from the bathroom, the method comprising:
   mounting a support structure on the door;
   attaching a first housing to the support structure proximate the interior surface of the door, the first housing supporting a motion detector sensor;
   positioning the motion detector sensor wherein the motion detection sensor defines a detection zone extending over the toilet and having a lower boundary spaced above the toilet wherein the patient seated on the toilet will be located below the detection zone without intruding into the detection zone and when the patient rises from the toilet the patient will enter the detection zone;
   attaching a second housing to the support structure proximate the exterior surface of the door, the second housing supporting an alarm device; and
   providing control circuitry to operably couple the motion detection sensor with the alarm device, the control circuitry configured to activate the alarm device when the motion detection sensor detects motion whereby a caregiver positioned outside the bathroom proximate the door with the door in the closed position will be notified by the alarm device when the patient rises from the toilet.

16. The method of claim 15 wherein the step of positioning the motion detector sensor includes selectively adjusting a vertical position of the motion detection sensor on the support structure.

17. The method of claim 15 wherein the step of positioning the motion detector sensor includes selectively adjusting an angular position of the motion detection sensor about a vertically extending yaw axis.

18. The method of claim 15 further comprising the step of selectively activating and de-activating the motion detection sensor, the alarm device and the control circuitry with a switch supported on the second housing.

19. The method of claim 15 wherein the step of mounting a support structure on the door includes engaging a portion of the support structure with a top edge of the door to mount the support structure on the door.

20. The method of claim 19 further comprising the step of extending wiring between the first and second housings to operably couple the motion detection sensor with the alarm device and wherein the wiring is extended over the top edge of the door.

* * * * *